US006231548B1

United States Patent
Bassett

(10) Patent No.: US 6,231,548 B1
(45) Date of Patent: May 15, 2001

(54) SECURING DEVICE FOR INTRAVENOUS CANNULA OR CATHETER

(76) Inventor: Alfred Ernest Bassett, 1 Aberfoyle Crescent, Suite 1102, Etobicoke, Ontario (CA), M8X 2X8

( * ) Notice: Subject to any disclaimer, the term of this patent is extended or adjusted under 35 U.S.C. 154(b) by 0 days.

(21) Appl. No.: 09/419,000

(22) Filed: Oct. 19, 1999

(30) Foreign Application Priority Data

Aug. 26, 1999 (CA) .................................................. 2281457

(51) Int. Cl.[7] .................................................. A61M 5/32
(52) U.S. Cl. .................................. 604/174; 128/DIG. 26
(58) Field of Search .................................. 604/174, 177, 604/179, 180, 304, 308; 128/DIG. 6, DIG. 26

(56) References Cited

U.S. PATENT DOCUMENTS

| 3,640,275 | * | 2/1972 | Burke et al. ........................... | 128/214 |
| 3,670,727 | * | 6/1972 | Reiterman ........................... | 128/214 R |
| 4,516,968 | * | 5/1985 | Marshall et al. ....................... | 604/174 |
| 4,679,553 | | 7/1987 | Proulx ................................... | 128/133 |
| 4,698,057 | * | 10/1987 | Joishy .................................. | 604/176 |
| 4,737,143 | | 4/1988 | Russell ................................ | 604/180 |
| 4,863,432 | * | 9/1989 | Kvalo ................................... | 604/177 |
| 5,306,253 | * | 4/1994 | Brimhall ............................... | 604/165 |
| 5,322,514 | * | 6/1994 | Steube et al. ......................... | 604/177 |
| 5,413,562 | * | 5/1995 | Swauger .............................. | 604/179 |
| 5,468,228 | | 11/1995 | Gebert ................................. | 604/174 |
| 5,578,013 | * | 11/1996 | Bierman .............................. | 604/180 |
| 5,643,217 | * | 7/1997 | Dobkin ................................ | 604/180 |
| 5,827,230 | | 10/1998 | Bierman .............................. | 694/174 |
| 6,074,379 | * | 6/2000 | Prichard .............................. | 604/524 |

FOREIGN PATENT DOCUMENTS

80/01458 * 7/1980 (WO).
WO 91/16939 * 11/1991 (WO).

* cited by examiner

Primary Examiner—Richard K. Seidel
Assistant Examiner—Cris Rodriguez

(57) ABSTRACT

An anchoring device for a catheter or cannula including a retainer section forming a channel extending along a central, longitudinal axis and a longitudinal slot along a top of the channel through which an elongate fluid carrying tube for the catheter or cannula can pass. This section includes one or more stop members projecting into the channel for engaging a radially extending surface of a line coupler for the catheter or a catheter connector. A flexible anchor pad is integrally connected to the retainer section and has top and bottom surfaces. A number of parallel ridges are distributed over the bottom surface of this pad to allow air between the pad and the skin of a patient. Preferably the anchoring device has an interior surface at the front end of the channel which frictionally engages the line coupling for the catheter in order to hold same. There is also disclosed a unique method of securing a catheter or cannula using this anchoring device.

9 Claims, 4 Drawing Sheets

SECURING DEVICE FOR INTRAVENOUS CANNULA OR CATHETER

BACKGROUND OF THE INVENTION

This invention relates to securing devices or anchoring devices for holding in place an intravenous cannula or catheter and the connection thereto.

There has been a continuing problem in the field of medical treatment with respect to administering intravenous medicinal fluids such as drip feed, anaesthetics and T. P. N. (Total Parenteral Nutrition) through tubing to an intravenous cannula or catheter. It is necessary to hold the cannula connector or connecting portion firmly in place on the patient's skin in order to prevent the cannula from being displaced or moved as a result of movement by the patient or movement of the flexible plastic tube that is connected to the line connector. Improper or inadvertent movement of the cannula can cause undesirable vein breakdown known as thrombophlebitis, requiring the placement of a new cannula at a different site on the patient. The replacement of the cannula can cause additional pain and suffering for the patient.

A well known and common means for securing the cannula connector and the cannula at the puncture site is to apply hypoallergenic plastic tape over the connector often in "chevron" configuration. It can be applied over the usual site dressing, commonly a product called "Opsite".

Various attempts have been made to develop and produce a better means for securing the cannula and its tube connector in place at the puncture site. One such known device is that taught in U.S. Pat. No. 5,413,562 issued May 9, 1995 to J. L. Swauger. This stabilizing fitting has a unitary pliable plastic body that has a centrally located catheter hub/syringe body retainer and two outwardly disposed support members, each of which is covered on its upper surface by hook type Velcro fastener. In order to hold this fitting in place on a person's wrist, a separate Velcro strap must be employed. This patent specification teaches away from the use of skin-contacting adhesive for securing purposes.

More recent U.S. Pat. No. 5,827,230 issued Oct. 27, 1998 to Venetec International Inc. describes a catheter anchoring system that includes a flexible, adhesive coated anchor pad which supports both a flexible tube clip and a retainer for the catheter needle. The retainer includes an upwardly open groove configured to receive an adaptor for the catheter and having a plurality of lateral slots, each sized to capture a radially extending annular rib of the adaptor to prevent the adaptor from sliding within the channel. Unfortunately, this device is reasonably complex in its operation and it requires the use of the special adaptor, including a coupling section with one or more annular ribs, this coupling section possibly including a leur lock type fitting.

One disadvantage of the known prior art securing devices is that with extended use on a patient they can create skin initation or rashes, either due to the creation of pressure points on the skin which can be quite sensitive or because they block off air from the skin for an extended period of time. It would be advantageous if the securing device for the catheter and its connector is constructed so as to reduce or minimize the amount of contact with the patient's skin and so as to enable air to pass along and be in contact with the skin.

It is an object of the present invention to provide an improved anchoring device for a catheter or cannula that is relatively simple to use and that can be made at a reasonable cost.

It is a further object of the invention to provide an anchoring device for a catheter that is both capable of securely holding the catheter in place while reducing the amount of discomfort for the user of the device.

SUMMARY OF THE INVENTION

According to the invention, an anchoring device for a catheter or cannula includes a retainer section having a channel extending along a central longitudinal axis thereof and a longitudinal slot along the top of the channel through which an elongate fluid carrying tube for the catheter can pass. The channel includes a central region of substantially uniform width. The retainer section also has at least one stop member projecting into the central region of the channel for engaging a radially extending surface of the line coupling element of the catheter or cannula and spaced from a rear end of the retainer section. The retainer section also has an inwardly tapering region close to its front end and a relatively narrow front end region. An interior surface of the front end region frictionally engages the line coupling element for the catheter in order to hold same in the channel. The anchoring device further includes a flexible anchor pad fixedly connected to a bottom side of the retainer section.

In a preferred embodiment, there are three stop members projecting into the channel for engaging the radially extending surface.

According to a further aspect of the invention, a method of securing a catheter, cannula and the like to the skin of a patient includes injecting a catheter or cannula needle into the patient at a desired location and connecting a line coupling element thereto. The coupling element has a relatively long fluid delivery tube connected thereto at an end opposite the catheter needle. The above described anchoring device is provided and the fluid delivery tube is inserted through the slot thereof so that the delivery tube extends along the channel. Then the anchoring device is moved generally in the direction of the central longitudinal axis of the channel towards the catheter needle in order to insert the line coupling element into the channel of the retainer section and to engage a radially extending surface thereof against the at least one stop member. The anchor pad is then secured against the skin of the patient with adhesive tape which extends over the top surface of the anchor pad.

Preferably during the aforementioned securing step, three strips of tape are extended over the top surface of the anchor pad, these strips being located at the sides of the retainer section and across the front thereof.

Further features and advantages will become apparent from the following detailed description taken in conjunction with the accompanying drawings.

DETAILED DESCRIPTION OF PREFERRED EMBODIMENTS

Figure 1:
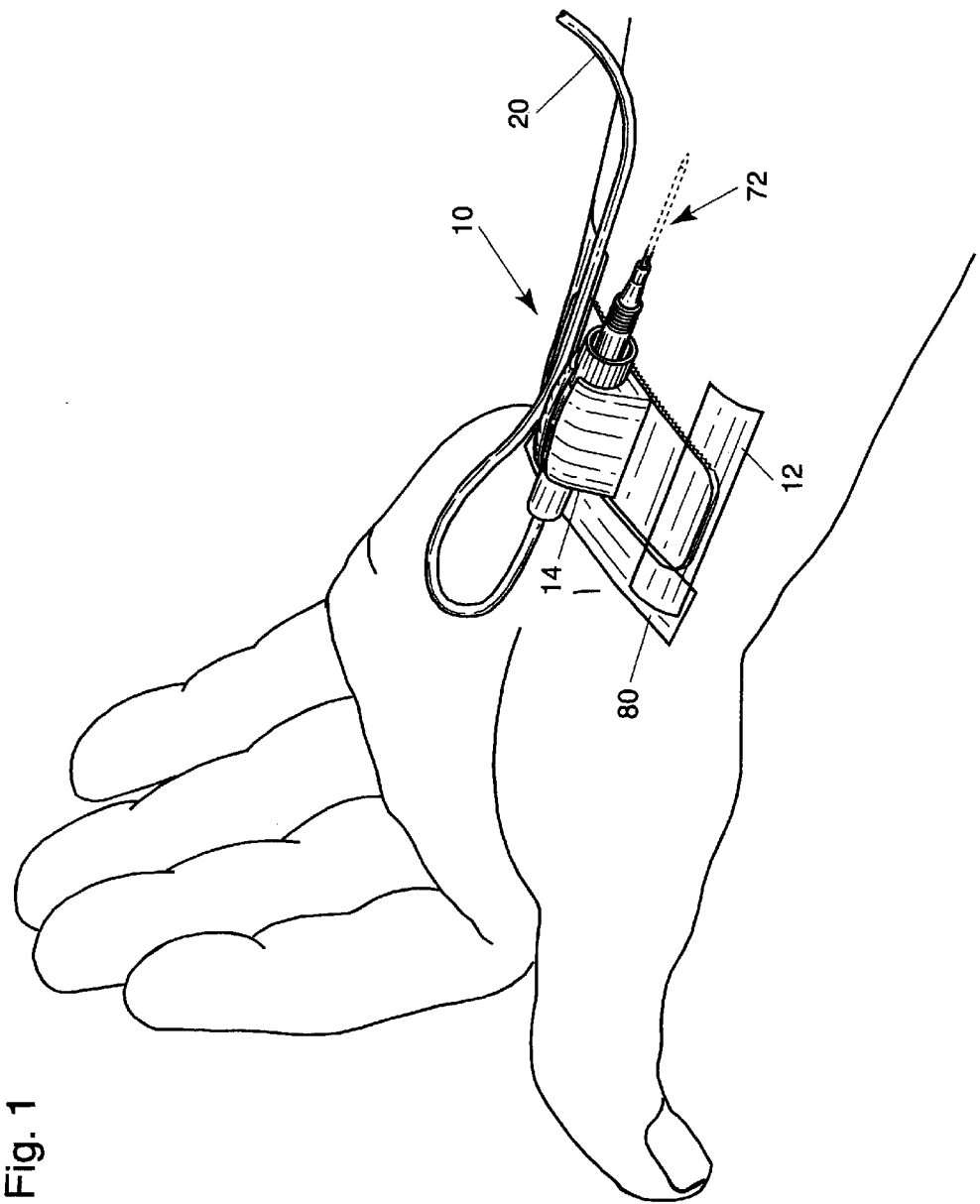
FIG. 1 is a perspective view showing how the anchoring device can be used to firmly attach an intravenous line to a person's arm.

A preferred form of anchoring device 10 for a catheter or cannula is shown attached by adhesive tape 12 and 80 to the wrist of a patient in FIG. 1. The preferred device includes a retainer section 14 forming a channel 16 extending along a central longitudinal axis indicated by the line A in FIG. 2. A longitudinal slot 18 extends along a top of the channel and has a width W which is less than the diameter of the channel. It will be understood that the slot 18 is made wide enough to permit an elongate fluid carrying tube 20 to be passed readily therethrough during the procedure for anchoring the catheter or cannula and its line connector in place.

The anchoring device 10 further includes a flexible anchor pad 22 having a top surface 24 and a bottom surface 26. The retainer section 14 is rigidly mounted and preferably integrally attached to the anchor pad 22 on its top surface. A number of protuberances are preferably distributed over the bottom surface of the anchor pad 22 to allow air between the anchor pad and the skin 28 of a patient during use of the anchoring device 10. The illustrated preferred protuberances comprise a series of closely spaced, parallel ridges 30 which can be small V-shaped ridges as shown separated by small V-shaped grooves 32. The parallel elongate protuberances ridges 30 cover substantially all of the bottom surface of the anchor pad 22 and, in any event, it is preferably that these ridges or the protuberances cover all of that portion of the bottom surface which comes into contact with the skin of the patient. As illustrated, the parallel ridges extend in a direction substantially parallel to the central longitudinal axis A or, in other words, perpendicular to the length of the anchor pad 22. Although the ridges could extend in other directions, for example, lengthwise of the pad, the illustrated direction is preferred in order to provide the pad with maximum flexibility, thus permitting it to bend readily in a direction perpendicular to the plane of the pad 22. This bending of the pad is indicated by the arrows B in FIG. 7. Thus, in the location of the pad shown in FIG. 1, the pad is readily able to flex in order to follow closely the transverse contour of the wrist. Although only the use of ridges 30 is illustrated, it will be understood that the protuberances can take various forms including a grid work of small bumps or disks and the use of short ridges interrupted by regularly spaced gaps across the width of the pad.

Figure 2:
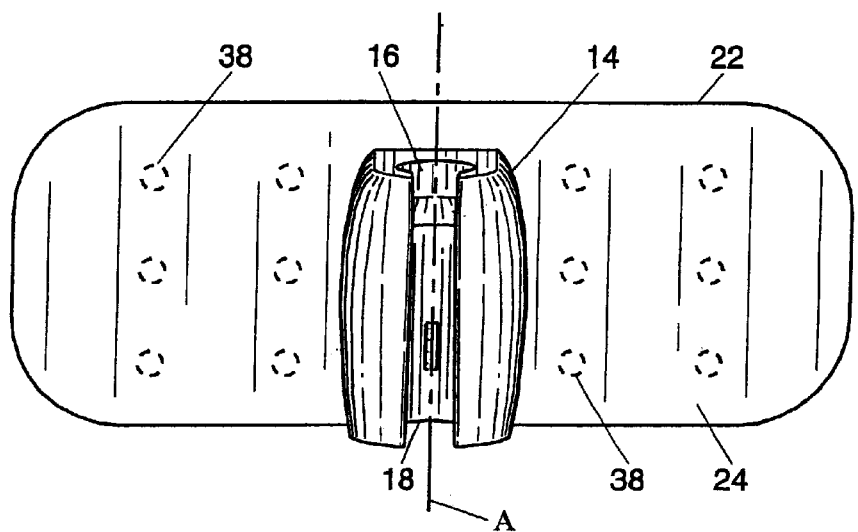
FIG. 2 is a top view of the anchoring device.
Figure 3:
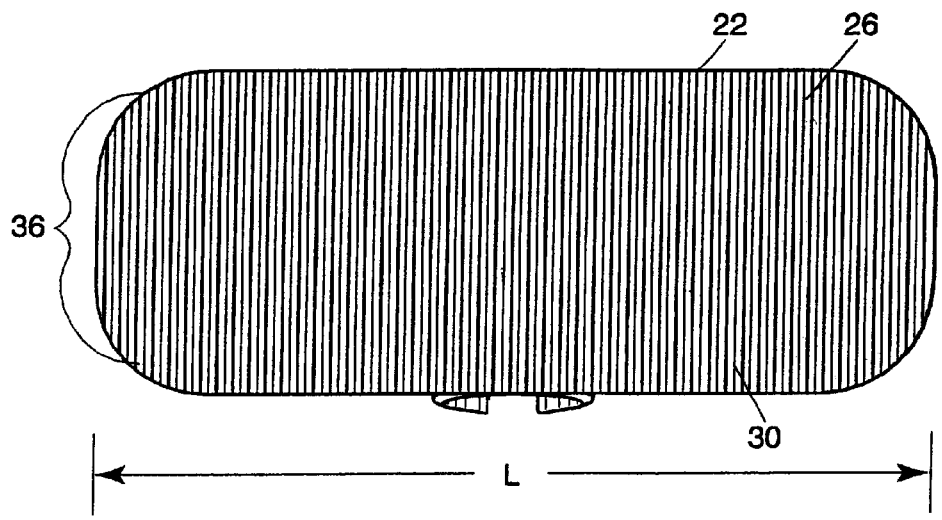
FIG. 3 is a bottom view of the anchoring device.
Figure 4:
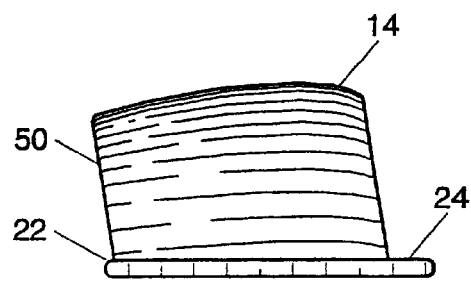
FIG. 4 is an end view of the anchoring device.

The preferred illustrated anchor pad is substantially rectangular having a length L of about 2 inches and a width of approximately 1 inch. The length of the pad extends perpendicularly to the central longitudinal axis A. Preferably the anchor pad has rounded corners 36 in order to avoid pressure points against the patient's skin which may be quite tender. In order to provide further aeration, a number of small holes 38 indicated in dash lines only in FIG. 2 can be formed in the pad and distributed over its surface. Although only a few such holes are shown in FIG. 2, it will be appreciated that a larger number of holes can be provided in the pad, if desired. A preferred version of the pad has a thickness of 15 to 50 thousandths of an inch measured from the top surface 24 to the bottom of the grooves. The thickness of the pad can vary depending on such factors as the type of plastic used and the application of the particular anchoring device. A more brittle plastic, such as an acrylic, can require a thicker pad in order to prevent inadvertent breakage. The height of the ridges can vary from 5 to 10 thousandths of an inch.

The preferred construction of the retainer section 14 will now be described with particular reference to FIGS. 5 to 8. The retainer section 14 has a base portion 40 and two upwardly extending curved sidewalls 42 and 44. The top edges of the sidewalls are spaced apart by the aforementioned slot 18. The substantially cylindrical channel 16 formed between the sidewalls extends the complete length of the retainer section from a front end 48 to a rear end 50, with the rear end 50 being the end positioned closest to the cannula needle. As can be seen from FIG. 9 wherein the central longitudinal axis of the channel is indicated by the dash line A, the channel extends at a small acute angle to the top surface 24 of the anchor pad. As shown in the drawings, this top surface is substantially planar when the anchoring device is formed and ready to use. In a particularly preferred embodiment, this small acute angle is in the range of 7 to 10 degrees with the low point of the central longitudinal axis located at the rear end 50 and the high end (the end furthest from the anchor pad) being located at the front end 48. The slope of the channel helps to ensure that the line connector and the cannula are supported at the correct angle as it is necessary for the cannula to enter the patient's skin at the proper angle and it should be held in this position. This slope also can lift a leur fitting or hub (see item 64 in FIG. 9) off the skin, helping to relieve or avoid a pressure point for the patient.

The preferred illustrated channel 16 has a relatively wide central region 54 which can be of uniform diameter and an inwardly tapering region 56 close to the front end 48. There is also a relatively narrow front end region 58 which can be of uniform diameter and which is much shorter in its length than the central region. As explained further hereinafter, a frictional engagement of a line coupling 60 for the catheter preferably occurs in the front end region 58.

Figure 9:
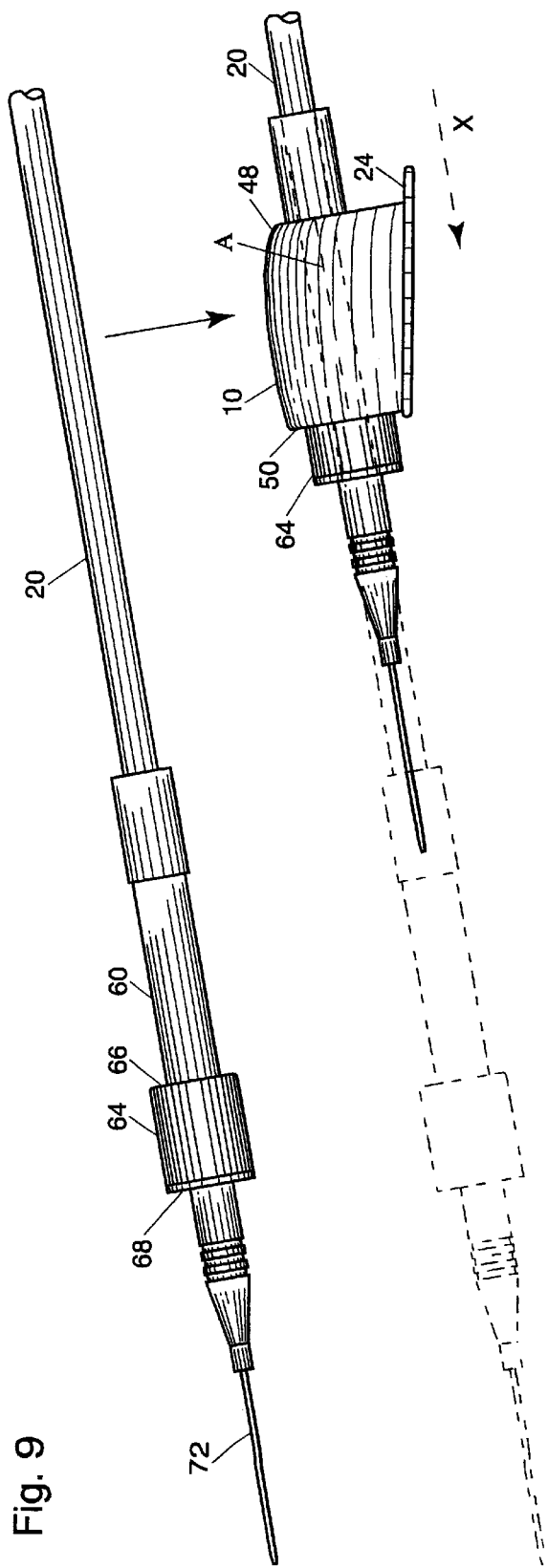
FIG. 9 is a side view showing a cannula and line connector being fitted into the anchoring device.

In addition to the aforementioned regions, the channel also has a short rear end region 62 which again can be of uniform diameter and in the illustrated embodiment has a diameter the same as the central region 54 of the channel. The diameter of this rear end region is about the same as the aforementioned leur hub 64 of the cannula. As shown in FIG. 9, this leur hub is generally cylindrical and has a radially extending end surface at 66 and an opposite end at 68. This leur hub 64 can be part of a standard line coupling for the catheter or cannula.

Figure 5:
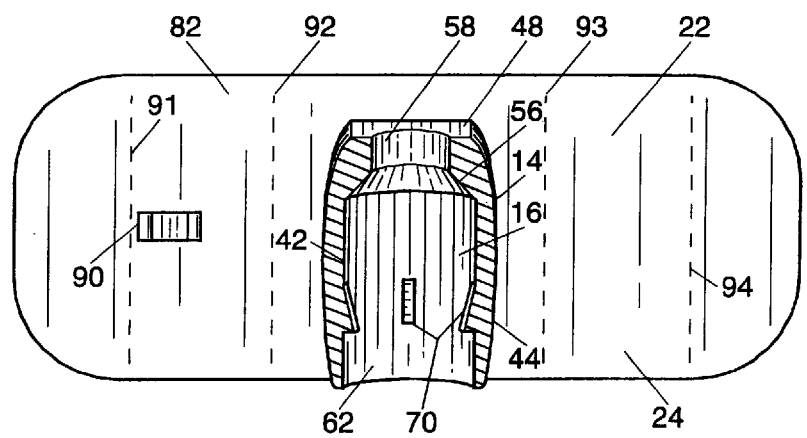
FIG. 5 is a sectional view taken along the line 5—5 of FIG. 8.
Figure 6:
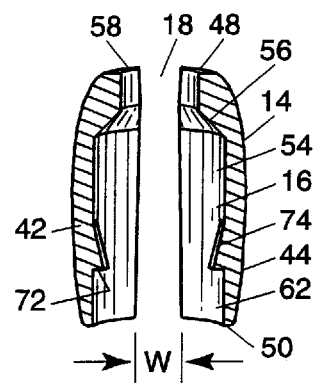
FIG. 6 is a sectional view taken along the line 6—6 of FIG. 7.

Located within the channel 16 are means for engaging and holding a connecting portion of the catheter such as the aforementioned leur hub 64. The preferred engaging and holding means includes at least one stop member 70 which may take the form of an integral, sloped catch member that projects into the channel and that is spaced from an adjacent end (referred to herein as the rear end 50 of the retainer section). The illustrated preferred retainer has three of these stop members 70 with one located centrally of the base portion and the other two located opposite one another on the side walls 42, 44. The preferred stop member 70 has a short, radially extending side 72 and a longer sloping side 74 that extends at a small acute angle to the central longitudinal axis A of the channel. It will be understood that the short end wall 72 engages against the end surface 66 of the leur hub when the line connector is fully inserted into the anchoring device. Instead of the three stop members shown, it is also possible to use an elongate ridge extending about the circumference of the channel with this ridge having a transverse cross-section corresponding to the shape of the stop members 70 as shown in FIGS. 5 and 6.

The preferred anchoring device is injection molded as a single, integral unit that includes both the retainer section 14 and the anchor pad 22. It is made from a suitably flexible, inexpensive plastic such as polyethylene but it will be understood that other types of plastic such as polystyrene and an acrylic plastic are also possible materials. Also, the preferred plastic material should be relatively clear or transparent so that the medical personnel using the device will be able to see through the device during use thereof to support a catheter or a cannula. Preferably, the interior surface of the retainer section 14 has a truncated circular cross-sectional shape as shown so that the channel 16 surrounds at least a portion of the line coupling element 60 through an arc of greater than 180 degrees about the central longitudinal axis A.

The preferred method of securing a catheter or cannula to the skin of a patient will now be described with particular reference to FIGS. 1 and 9 of the drawings. Firstly, the catheter needle or cannula is injected into the patient at a desired location which could be the patient's wrist, as shown in FIG. 1, or in some other location such as further up on a person's arm, etc. At this time a line coupling element such as a line coupling 60 with a leur hub 64 is connected to the catheter needle and to this coupling element there is connected a relatively long fluid deliver tube 20, which is connected at an end opposite the catheter needle. Generally a suitable known site dressing, such as the product called "Opsite" would be used at this stage to help secure the catheter needle in place. Then, in order to attach the anchoring device 10, the flexible plastic tube 20 is pushed through the elongate slot 18 so that this tube extends along the channel 16. The anchoring device 10 can then be moved easily along and below the flexible plastic tube as suggested by the arrow X in FIG. 9 and then the narrower portion of the line coupling 60 can be brought through the channel 16 as well. In other words, the anchoring device 10 is moved generally in the direction of the central longitudinal axis A of the channel towards the catheter needle 72 in order to insert the line coupling 60 into the channel and then to engage the rearwardly extending surface 66 of the leur hub, which is part of the line coupling element. This rearwardly extending surface is brought to a position against the stop members 70 at which point further movement of the anchoring device along the line connector is prevented. It will be appreciated that at this stage the interior surface of the channel in the front end region 58 preferably frictionally engages the line coupling in order to hold same in the channel. In the preferred embodiment, the amount by which the leur hub extends into the channel is between about ³⁄₁₆ths and ¼ inch.

Once the anchoring device 10 has been brought to this position relative to the line coupling, the anchor pad is secured to the skin of the patient with the aforementioned adhesive tape 12 which extends over the top surface of the anchor pad. At least two strips of tape 12 (only one of these strips 12 is shown in FIG. 1) extend across the top surface of the anchor pad in order to secure the anchoring device to the skin. The strip of tape 12 (not shown in FIG. 1) is positioned in the same manner as the illustrated tape but is located at the opposite end of the anchor pad. Preferably, a further section of tape 80 is attached to the anchor pad perpendicular to the two tapes 12 along the front edge section 82 of the anchor pad to provide for a more secure attachment. This additional tape can extend at least the entire length (ie. 2 inches) of the anchor pad. The preferred tapes 12 and 80 to be used for this purpose are a standard paper-like hypoallergenic plastic tape such as the type which has been used in the past to secure in place a catheter or cannula.

It will be understood that the flexible plastic line 20 shown in the drawings can be connected in the usual manner to a container, such as a plastic bag, containing a prescribed drug or T.P.M. The drug or nutritional fluid is fed through the line 20 by gravity in order to enter the patient intravenously. It will be appreciated that the dimensions of and shape of the anchor pad 22 can be varied and may be varied to suit the particular application it is intended for. For example, though the illustrated anchor pad is suitable for use on the wrist of many patients, an anchor pad with a square shape and having dimensions of about 1.5 inches may be more suitable for use on a patient's upper arm which is larger than the wrist area.

Figure 7:
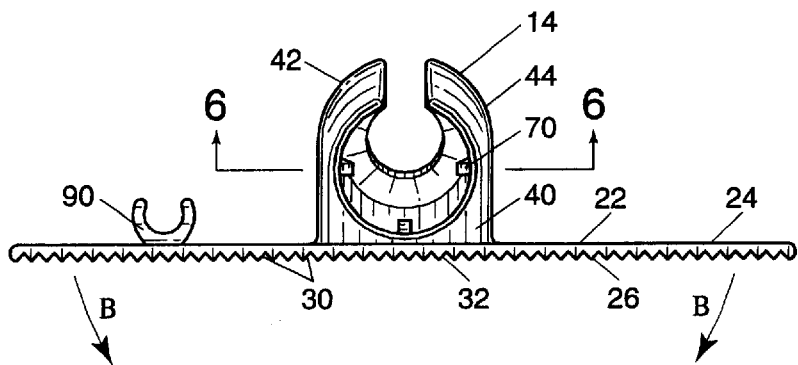
FIG. 7 is a rear end view of the anchoring device.
Figure 8:
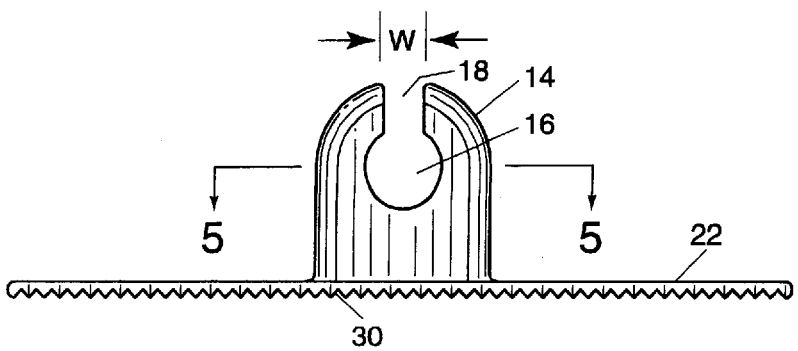
FIG. 8 is a front end view of the anchoring device.

If desired and as shown in FIG. 5 and 7, the upper surface of the anchor pad can have formed thereon a side clip 90 to provide a means for holding the flexible plastic tube in a bent back position. It is also possible to provide two or more score lines 91 to 94 extending transversely across the anchor pad as illustrated in FIG. 5. These are lines of perforations or weakened areas so that the pad will bend more easily to the user's skin contour.

In the version of FIG. 5, two of these scorelines are provided across each end section of the pad.

It will be seen by those skilled in this art that the present invention provides an anchoring device which is both simple in its design and in its manner of use and which also provides a very firm connection of the cannula or catheter and its connector to the patient's body. The preferred anchoring device can be attached to a standard line connector for the cannula and, when used, it reduces the impact of any tugging or twisting on the flexible plastic tubing or on the line connector itself, which tugging or twisting can result in displacement or movement of the needle and a resulting need to replace the needle and related items at a significant cost. With the use of the present anchoring device, a patient will experience less needle replacement and will also have more freedom of movement while undergoing I.V. therapy. A further benefit is provided to the care giving facility or those organizations funding health care as the use of the present invention will save nursing time and will reduce the need to replace all of the disposable items such as the tubing, the needles, the line connectors, the tape, etc.

It will be appreciated by those skilled in the art that various modifications and changes can be made to the described anchoring device without departing from the spirit and scope of this invention. Accordingly, all such modifications and changes as fall within the scope of the appended claims are intended to be part of this invention.

I claim:

1. An anchoring device for a catheter, or cannula comprising:

a retainer section having a channel extending along a central longitudinal axis thereof, said channel including a central region which has a substantially uniform width and is relatively wide, a longitudinal slot along a top of said channel through which an elongate fluid carrying tube for said catheter or cannula can pass, at least one stop member projecting into said central region of said channel for engaging a radially extending surface of a line coupling element of said catheter or cannula and spaced from a rear end of the retainer section, an inwardly tapering region close to a front end of the retainer section, and a relatively narrow front end region, wherein an interior surface of said front end region frictionally engages said line coupling element of said catheter or cannula in order to hold same in said channel when the device is in use; and a flexible anchor pad fixedly connected to a bottom side of said retainer section and having top and bottom surfaces, wherein said retainer section is located adjacent a central section of said top surface of the anchor pad.

2. An anchoring device according to claim 1 wherein there are three stop members projecting into said channel for engaging said radially extending surface.

3. An anchoring device according to claim 1 wherein said flexible anchor pad has a series of parallel elongate protuberances extending over its bottom surface to allow air between said anchor pad and the skin of a patient during use of said anchoring device.

4. An anchoring device according to claim 1 wherein said device is molded from flexible plastics material as a single integral unit that includes the retainer section and the anchor pad.

5. An anchoring device according to claim 1 wherein a longitudinal centerline of said channel extends at a small acute angle to said top surface of the anchor pad, said top surface being substantially planar when said anchoring device is formed and ready to use.

6. An anchoring device according to claim 5 wherein said interior surface of said retainer section has a truncated circular cross-sectional shape so that the channel surrounds at least a portion of said line coupling element through an arc of greater than 180 degrees about said longitudinal centerline of said channel when the device is in use.

7. A method of securing a catheter, or cannula to the skin of a patient, comprising:

injecting a catheter or cannula needle into the patient at a desired location and connecting a line coupling element thereto, said coupling element having a relatively long fluid delivery tube connected thereto at an end opposite said catheter or cannula needle, providing an anchoring device comprising a retainer section having a channel extending along a central longitudinal axis thereof, said channel including a central region of substantially uniform diameter, a longitudinal slot along a top of said channel through which an elongate fluid carrying tube for said catheter or cannula can pass, and at least one stop member projecting into said control region of said channel for engaging a radially extending surface of a line coupling element of said catheter or cannula and spaced from a rear end of the retainer section, wherein a front end portion of an interior surface of said channel extends closely about said line coupling element for said catheter or cannula in order to hold same in said channel and prevent sideways or upward movement thereof during use of the anchoring device, and a flexible anchor pad fixedly connected to a bottom side of said retainer section;

inserting said fluid delivery tube through said slot so that the delivery tube extends along said channel;

moving said anchoring device generally in the direction of said central longitudinal axis towards the catheter or cannula needle in order to insert said line coupling element into the channel of the retainer section and to engage a radially extending surface of said line coupling element against said at least one stop member; and then securing said anchor pad on the skin of the patient with adhesive tape which extends over said top surface of the anchor pad.

8. A method of securing a catheter according to claim 7 wherein in said securing step, strips of tape are extended over said top surface, said strips being located on opposite sides of said retainer section and along a front edge portion of said anchor pad.

9. A method of securing a catheter according to claim 8 wherein during said moving step, the interior surface of said retainer section at at least a front end thereof is caused to frictionally engage said line coupling element in order to hold same in the channel.

* * * * *